US008127595B2

(12) United States Patent
Finlay et al.

(10) Patent No.: US 8,127,595 B2
(45) Date of Patent: Mar. 6, 2012

(54) PRE-CONCENTRATOR AND SAMPLE INTERFACE

(75) Inventors: Alan Finlay, Richmond (GB); Eric Yeatman, London (GB); Steven Wright, Horsham (GB)

(73) Assignee: Microsaic Systems PLC, Woking, Surrey (GB)

( * ) Notice: Subject to any disclaimer, the term of this patent is extended or adjusted under 35 U.S.C. 154(b) by 718 days.

(21) Appl. No.: 12/284,778

(22) Filed: Sep. 25, 2008

(65) Prior Publication Data
US 2009/0090197 A1 Apr. 9, 2009

(30) Foreign Application Priority Data
Oct. 4, 2007 (GB) .................................. 0719397.2

(51) Int. Cl.
*G01N 1/22* (2006.01)
*G01N 1/40* (2006.01)
*G01N 30/02* (2006.01)
(52) U.S. Cl. ..................... 73/31.07; 73/23.41; 73/863.12
(58) Field of Classification Search ................. 73/31.07, 73/23.41, 863.12, 61.55, 61.59, 64.56, 863.21, 73/863.23, 864.34
See application file for complete search history.

(56) References Cited

U.S. PATENT DOCUMENTS
4,293,316 A * 10/1981 Block ....................... 73/31.07 X
(Continued)

FOREIGN PATENT DOCUMENTS
GB 2434643 A 8/2007
(Continued)

OTHER PUBLICATIONS
Mitra, Somenath et al., "Continuous Gas Chromatographic Monitoring of Low Concentration Sample Streams Using an On-Line Microtrap," *Journal of Chromatography*, 648 (1993) 415-421.
(Continued)

*Primary Examiner* — Thomas P Noland
(74) *Attorney, Agent, or Firm* — Bishop & Diehl, Ltd.

(57) ABSTRACT

This invention describes a multi-stage pre-concentrator device for use with a detector system. One pre-concentrator stage is detachable and may be used to collect sample remotely from the detection system. The detachable pre-concentrator stage mates with the detector system and can transfer its desorbed sample to another pre-concentrator stage which also incorporates the functions of a sample loop serving as an injection volume to the separation column of an analytical instrument. In one embodiment the fixed pre-concentrator stage serves as a sample loop that preferably integrates suitable valves with sorbent materials onto the same structure to minimise dead volume, maximise sensitivity, improving column loading efficiency, reducing duty cycles and minimising detection system response time.

30 Claims, 17 Drawing Sheets

U.S. PATENT DOCUMENTS

| | | | |
|---|---|---|---|
| 5,083,019 | A | 1/1992 | Spangler |
| 5,109,691 | A | 5/1992 | Corrigan et al. |
| 5,481,110 | A | 1/1996 | Krishnaswamy et al. |
| 5,585,575 | A * | 12/1996 | Corrigan et al. ....... 73/863.21 X |
| 6,112,602 | A | 9/2000 | Mitra |
| 6,171,378 | B1 | 1/2001 | Manginell et al. |
| 6,244,117 | B1 | 6/2001 | Mengel et al. |
| 6,345,545 | B1 | 2/2002 | Linker et al. |
| 6,914,220 | B2 | 7/2005 | Tian et al. |
| 7,524,363 | B2 * | 4/2009 | Bentley et al. .................. 96/101 |
| 7,980,147 | B2 * | 7/2011 | Tang ...................... 73/863.21 X |
| 2004/0035185 | A1 | 2/2004 | Allen |
| 2005/0095722 | A1 | 5/2005 | McGill et al. |
| 2007/0034024 | A1 | 2/2007 | Syage |
| 2011/0133070 | A1 * | 6/2011 | Taylor et al. .................. 250/282 |

FOREIGN PATENT DOCUMENTS

WO    WO 2006/062906 A1    6/2006

OTHER PUBLICATIONS

Feng, Chaohua et al., "Two-Stage Microtrap as an Injection Device for Continuous On-Line Gas Chromatographic Monitoring," *Journal of Chromatography, A* 805, 1998, pp. 169-176.

Tian, Wei-Cheng et al., "Microfabricated Preconcentrator-Focuser for a Microscale Gas Chromatograph," *Jounral of Microelectromechanical Systems*, vol. 12, No. 3. Jun. 2003. pp. 264-272.

2 pages from British Search Report for corresponding application, Date of search Feb. 3, 2008.

European Search Report for related European Application No. 081655060.0 dated Apr. 22, 2009.

* cited by examiner

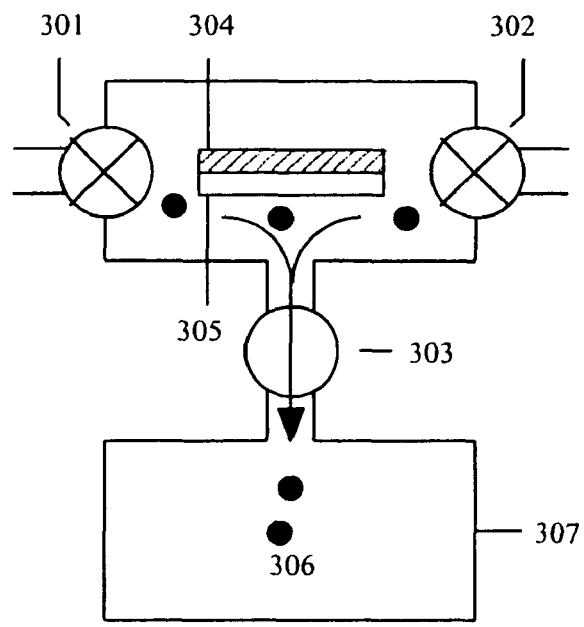
Figure 3.                                                    Prior Art
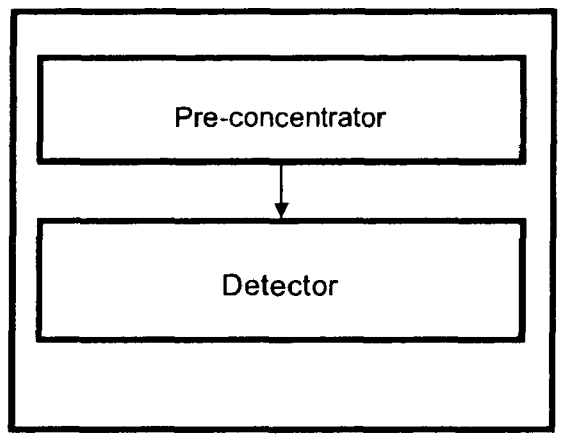
Figure 4.                                                    Prior Art

PRE-CONCENTRATOR AND SAMPLE INTERFACE

CROSS-REFERENCE TO RELATED APPLICATIONS

This application claims priority to United Kingdom Application GB0719397.2, filed Oct. 4, 2007, which is hereby incorporated by reference.

FEDERALLY SPONSORED RESEARCH OR DEVELOPMENT

Not Applicable.

TECHNICAL FIELD

The invention relates to multi-stage pre-concentrator devices for use with detector systems. In particular, the invention provides for a detachable pre-concentrator stage that operatively mates with a detector system and can transfer a collected species of interest to another pre-concentrator stage which may also incorporate the functions of a sample loop serving as an injection volume to the separation column of an analytical instrument.

BACKGROUND OF THE INVENTION

Portable chemical detector systems are required for the detection of explosives and other hazardous material. Such systems may be based on separation by gas chromatography followed by detection using a mass spectrometer, or on ion mobility spectrometry, or on mass spectrometry alone. Because the ambient concentration of the target analyte of interest is vanishingly low, other devices are often incorporated to improve the limit of detection. One such device is a chemical pre-concentrator, a device for boosting the concentration of an analyte of interest in a stream prior to analysis by a detector.

Exemplary components of a known pre-concentrator system are shown in FIG. 1. The pre-concentrator element itself is in essence a trap that will preferentially sorb a dilute analyte from a gas or liquid stream. Within the context of the present invention a sorbent material is one that will sorb a sample from a fluid—be that in the liquid or gaseous phase. To sorb is to take up a liquid or a gas either by adsorption or by absorption. Sorption is often enhanced by the use of a porous material or a chemically reactive layer of material. Examples of the former are carbon granules and sol-gel glasses, and examples of the latter are functionalised polymers. This material 101 is held on a mechanical support 102, which can be heated. Usually heating is carried out electrically, in that the passing of a current through the support 102 provides a corresponding heating of the support 102.

The trap is placed in a small enclosure 103 between three valves. The first valve 104 connects to a gas flow input 105, and the second valve 106 connects to a gas flow output 107. The third valve 108 connects to a subsequent analysis system 109. Pre-concentration typically involves a repetition of sorption and desorption steps.

FIG. 2 shows an example of a sorption step. The input and output gas flow valves 201 and 202 are opened, and the valve 203 connecting to the analysis system is closed. A gas stream 204 containing a small fraction of the target analyte 205 together with a large fraction of other gas molecules 206 is allowed to pass over or through the trap. Most of the analyte 207 is sorbed on the trapping layer 208, while the remainder of the gas stream is vented as exhaust 209.

FIG. 3 shows a corresponding desorption step. The input and output gas flow valves 301 and 302 are closed, and the connecting valve 303 is opened. The sorbed molecules are desorbed, usually by rapidly raising the temperature of the chemically sensitive layer 304 using the heater 305, and a concentrated flux of the analyte of interest 306 is passed into the analysis system or detector 307.

FIG. 4 shows in schematic form a detector system incorporating a pre-concentrator. Such systems including macroscopic pre-concentrators are available commercially. Pre-concentrator performance is defined in terms of the efficiency (i.e., the fraction of the desired analyte that is retained) and of the concentration factor (i.e. the increase in the desired analyte concentration). To maximize the efficiency, the surface area of the trap should be large as possible, and the sensitised coating highly attractive to the desired analyte, while to maximize the concentration factor, dead volumes should be as small as possible.

To reduce cycle times, the heated element should have low thermal mass. However, to increase the concentration factor even further without increasing the time needed for desorption, pre-concentrators can be used in a cascade consisting of a first trap with a large volume followed by a second trap with a small volume. The first trap has high efficiency but a long desorption time while the second trap has a short desorption time. Pre-concentrators containing even more stages are constructed in an analogous way.

The above considerations suggest that pre-concentrators are ideal candidates for miniaturization, and small traps based on capillaries were developed in the 1990s (Mitra and Yun 1993; Feng and Mitra 1998; U.S. Pat. No. 6,112,602). Increased integration with other components such as valves and gas chromatographs can be achieved by planar processing, and several planar pre-concentrators with thin-film heaters have been developed (U.S. Pat. Nos. 5,481,110; 6,171,378). Micromachined heaters with deep, etched trays filled with sorbent granules have also been demonstrated (Tian et al. 2003; U.S. Pat. No. 6,914,220). A flow-though pre-concentrator based on a sorbent polymer coating on a perforated heater has also been developed (US 20050095722). None of these configurations is entirely suitable for a compact system, since the valves needed for overall operation are often added by hybrid integration, causing an increase in dead volume and a reduction in concentration factor. A planar micro-machined valve and thermal desorber is described for use as a pre-concentrator with the advantages of low dead volumes and a high concentration factor (Syms and Yeatman; GB 2434643A). However, as described this device may suffer from a limited flow rate of sample from the ambient air during the sorption cycle. Furthermore, all of these devices are designed to be permanently coupled to the detector system, compelling the user to carry the entire system to any location of interest. This is not always feasible or practical.

Detector systems featuring a single-stage pre-concentrator that is also detachable from the detector are known. In some Concepts of Operations (CONOPS), it may not be possible take the detector system to the sample, and instead the detachable pre-concentrator may be hand-carried to a remote location and used to collect sample. Species of interest are gathered by a sorbent material in the pre-concentrator, and trapped. Once the sufficient sample has been collected remotely, the detachable pre-concentrator may be returned to the detector and then coupled with the detector, whereon the species of interest is desorbed and transferred to the detector system for analysis. A system of this type has been developed (Barket; Patterson; Gregory 2004, WO2006062906) and is commercially available.

However, the hand-portable sample collection devices of the type disclosed have the disadvantage of being relatively expensive, bulky units which typically include pumps, sorbent tubes, valves and flow meters. The size and cost of these units limits their deployability. For example, a sample collection device with a weight of four pounds is excessive and cannot be given to every soldier unless it is at the expense of other equipment.

More importantly, for the sample collector disclosed in WO2006062906 and similar single stage pre-concentrators, there are difficulties in efficiently transferring the collected sample to the preferred analytical system, a gas chromatography mass spectrometer (GC-MS). These difficulties may increase the technical complexity of the analysis, increase the duration of the analysis, and lead to loss of potentially valuable sample.

Firstly, the flow of gas required to efficiently flush the analyte from the pre-concentrator during the desorption step may be much higher than can be directly accommodated by the GC column. When this is the case, the excess flow (containing valuable analyte) is discarded through the use of a splitter, thereby reducing the overall sensitivity. Alternatively, the pre-concentrator can be allowed to discharge through a conventional sample loop. However, this is again very wasteful, as the injected volume (typically 1-2 ml) will be a small fraction of the total volume of gas used to flush the pre-concentrator.

Secondly, the use of conventional pipe-work, unions, valves and other gas handling hardware introduces considerable dead volume into the system. During the desorption step, the analyte is therefore discharged into a much larger volume of carrier gas than might otherwise be desirable.

Thirdly, a typical GC system requires that the temporal profile of the injected analyte be of the order of a few seconds wide. When using direct injection, the mass of a conventional pre-concentrator is such that the sorbent cannot be heated fast enough to achieve such a narrow desorption profile, and as a result, a secondary refocusing step is generally required. In the case of involatile analytes, refocusing is achieved by trapping at the head of the column by using a suitably low column temperature whereas volatile analyte must be refocused using a cryotrap. Clearly, the provision of cryogenic materials in the field or to a portable GC is highly inconvenient.

There is therefore a need for improved detection systems.

SUMMARY OF THE INVENTION

These and other problems are addressed by the present invention in providing a multi-stage pre-concentrator system, at least one stage of which is a detachable pre-concentrator device which may be portable for remote sampling, the system including at least one other pre-concentration device having a region of fixed volume that traps analyte entering from the first-stage pre-concentrator using a suitable chemically sorbent material and that may also be configured to serve as an integrated sample loop by combining the two elements directly in a compact assembly with low dead volume. By providing such an arrangement, it is possible to provide for a trapping of ambient samples remotely using a portable pre-concentrator and to bring the sample so trapped to the detector, rather than vice versa. This has specific application in certain CONOPS, where the provision of a bulky detection system at the point of sample collection is not practical.

A first embodiment of the invention provides a multi-stage pre-concentrator system configured to provide for a detection of one or more species present in a gas flow. The system includes at least one detachable collection device ("the first stage") configured to provide for sorption of one or more species present in a gas flow, the first-stage device including a trap through which the gas may flow, entry of gas into the trap being provided through an orifice or other opening into the trap. Such an opening may be provided in a sealable configuration, be that through provision of a permanently breakable seal or a re-sealable entry port through use of, for example, a valve arrangement. However it will be appreciated that as this first stage is typically operable as a sample collector it is not essential to provide such levels of complexity as are typically required for a pre-concentrator. For example the first stage could be permanently open allowing free access to the sorbent material, but during periods of non-use the first stage is maintained in a separate sealable container preventing contamination of the sorbent material prior or subsequent to its use.

While all that is required is a fluid flow (gaseous or liquid) past the sorbent material, it is useful to have a regular flow and to provide such a regular flow stream the first stage will typically employ a fan or pump to provide a controlled flow of a sample fluid over a region containing some sorbent material. As was mentioned above, the trap is provided with a sorbent coating configured to selectively sorb the species present in the gas during the flow of gas through the trap. Optimally the trap can also be heated so as to effect desorption of the previously adsorbed species from the sorbent coating.

The first stage, which may be a detachable collection device, could be of relatively simple and inexpensive construction and therefore highly portable. In operational scenarios, a cheap, lightweight sample collection device of this kind could be deployed by attaching it to clothing, flak-vests, helmets and marching-order and so on. In this way, the collection device may be used for search of buildings, roads, vehicles and at checkpoints. By obviating the requirement for complex valve arrangements such a cheap, lightweight arrangement may be provided.

The system also includes at least one other collection device ("a second stage"), the second stage also including a trap through which the gas may flow, entry of gas into the trap through an orifice being controlled by a valve, which is moveable between a first position wherein the gas is free to move through the orifice and into the trap and a second position wherein the valve seals the orifice preventing the flow of gas into the trap, and wherein the trap is provided with an sorbent material configured to sorb the species present in the gas during the flow of gas through the trap, and wherein on sealing of the orifice the sorbent material is heatable so as to effect an desorption of the previously sorbed species from the sorbent coating.

Alternatively, during the flow of gas from the first-stage pre-concentrator device through into the trap of the second pre-concentrator stage, the species present in a gas is sorbed by the sorbent material in the trap during the trapping cycle, and the sorbent material retains the species of interest until instead of heating it is 'washed out' by stream of carrier fluid or solvent entering the trap from a reservoir during the discharge cycle.

In one embodiment, the second-stage pre-concentrator device may be as described in GB 2434643A, the content of which is incorporated herein by way of reference. By incorporation of a sorbent surface onto a membrane that seals the trap, it is possible to provide dual functionality of valve and sorbent material on the membrane. The membrane may be a moveable membrane in this embodiment, whereby it functions as a valve. Such dual functionality reduces the number of parts that are required for the sensor and also eases the control functionality required for operation of the device. Within the context of this embodiment of the invention it will be appreciated that the sorbent material could be provided as a layer or coating on the membrane or indeed could be provided as a second object that is integrally formed with the membrane or indeed sequentially added to the membrane.

The system is desirably configured to provide for detection of a chemical species, although it will be appreciated that a suitably defined sorbent surface, layer or material could provide for a detection of biological materials also, or instead of the chemical species.

Where the species to be detected is a chemical species, it is typically a volatile organic compound, explosive, chemical weapon or toxic industrial chemical.

The first stage may be assembled from commercial off the shelf technology (COTS) such as coarse dust filters, fans, pumps, printed circuit boards, gaskets, injection moulded plastic enclosures, batteries and a mesh or other suitable surface coated with a suitable sorbent material or coating. Where provided as a mesh, the mesh itself can be formed from a suitable material such as a metal, semiconductor, conductive polymer or conductive composite that may be rapidly heated resistively by application of an electrical current. To increase the contactable surface area of sorbent material exposed to a fluid flow without increasing the dimensions of the first stage, a trap in accordance with the teaching of the invention may employ a stacked collector arrangement whereby multiple layers of sorbent material are provided in a stack arrangement such that on passing a fluid (gaseous or liquid) through the stack more sorption is achieved than would be possible using a single layer arrangement.

In the first stage, the sorbent coating may be included from a suitable material as a coating on the mesh, other configurations or applications may provide for the formation of the mesh from a semiconductor, metal, polymer, ceramic or composite with sorbent properties. Where provided in a semiconductor, the coating may be provided by post-processing of the mesh by painting, ink jet printing, sputtering, plating or some other suitable process. The sorbent coating may be provided in typical embodiments by a porous material or a functionalised polymer. It will be appreciated that the exact nature of the sorbent material or coating will be defined by the species which is desired to be detected using the system.

In a preferred embodiment, the second-stage pre-concentrator provides in accordance with the teaching of GB 2434643A, a pre-concentrator device including a combined electrostatically operated valve and an electrically heated desorber, comprising a movable flap carrying a chemically selective coating which is suspended by an elastic element above an orifice in an insulated substrate. It will be understood however that the teaching of the invention is not to be unnecessarily limited to such a combination as the removable pre-concentrator may be used in combination with other examples of detector systems.

In operation, the first stage pre-concentrator may include a fan or pump which passes a continuous flow of dilute sample over the mesh. The mesh's sorbent coating selectively sorbs the chemical species of interest from the stream over a period of time, effectively 'integrating' the concentration of the analyte of interest.

It is likely that during sample collection using the first detachable stage, considerable quantities of contaminants such as water or diesel will become sorbed. As these chemicals are generally not of analytical significance and can be deleterious to the operation of the analytical instrumentation and subsequent data analysis, it is desirable to remove them before the charge of sorbed analyte is transferred to the second stage. This could be achieved by pre-heating the first stage to a moderate temperature with the fan blowing before it is coupled to the second stage.

The first stage, if not already attached to the system, is then inserted into, or attached to, the system once sample has been collected remotely. In various operational scenarios, personnel would return from searching a checkpoint, building, vehicle, road-side or field and 'dock', or otherwise mate or couple, the first stage device onto the system.

Once attached to the system, the first stage device mates with a second-stage collection device. The second stage also provides a pre-concentrator device comprising a trap defining an enclosure, the enclosure including at least three valves through which gaseous flow through the trap may be controlled. One of the three valves may, in one embodiment, be provided by the membrane with integrally formed sorbent coating, in which case two additional valves may be required.

The second stage may include a sealable orifice through which the gas stream may enter the trap. Such an orifice may be sealable by a valve, the valve configured to seal the trap on movement of the valve to a closed position. When this orifice is unsealed, the first stage is in fluidic communication with the second stage. The first stage mesh can then be heated, desorbing the collected species of interest from the first stage device and into the second stage. The pump or fan on the first stage device may be operated in reverse to promote flow of desorbed analyte into the second stage.

An opening of a first valve in the second stage provides for a flow of gas from the first stage and across the sorbent material within the second stage trap, and out through a second valve to an exhaust port, or to a pump. The pump may be coupled to the second valve to generate a negative pressure in the trap, promoting flow through the trap with the first valve open. The second stage trap then sorbs the relatively pure stream of species of interest from the first stage, before sealing by closing the first and second valves. The sorbent material of the second stage may then be heated to desorb the species of interest into the trapping volume of the second stage. The species of interest is now highly concentrated within the small volume of the trap. The closure of the first and second valves and the opening of a third valve will permit a concentrated 'slug' of analyte species to flow into a detector for analysis and identification.

In an alternative mode of operating this second stage device, the closure of the first and second valves, and the opening of the third valve along with a fourth valve connected to a reservoir, permits the injection of a mobile phase such as a purge gas, eluent or carrier fluid from the fourth valve through the trapping volume to transfer the analyte, which was desorbed from the heated material (or the case of a liquid carrier fluid, the analyte elutes from the material) into the trap as a highly concentrated 'slug' to an Ion Mobility Spectrometer (IMS), Mass Spectrometer (MS), separation system, chromatography column, Liquid Chromatography Mass Spectrometer (LC-MS), Gas Chromatography Mass Spectrometer (GC-MS) or some other analytical instrument, for subsequent analysis and identification. In this mode of operation the second stage pre-concentrator device also performs the function of a sample loop of fixed injection volume of the type commonly found on LC, GC, LC-MS and GC-MS systems (B. Kolb and L. S. Ettre, "Static Headspace-Gas Chromatography: Theory and Practice.").

The advantages of a multi-stage pre-concentrator, with the second stage incorporating the functions of pre-concentrator, include the result that valves and sample loop of fixed injection volume are low dead volumes, and high concentration factors, rapid heating and highly efficient loading of the chromatography column are achievable. In use with a GC-MS (gas chromatography-mass spectrometry) or LC-MS (liquid chromatography-mass spectrometry) system these advantages will give rise to very high sensitivity, rapid response times and short duty cycles—all factors which are of critical importance in operational use in the field.

These and other features and benefit will be understood with reference to the following exemplary embodiments.

BRIEF DESCRIPTION OF THE DRAWINGS

To understand the present invention, it will now be described by way of example, with reference to the accompanying drawings in which:

FIG. 3 shows the desorption step of chemical pre-concentration, as described in prior art.

FIG. 4 is a schematic showing the elements of a pre-concentrator detection system, as described in the prior art.

FIGS. 8($b$) and ($c$) show a stack of substrates separated from each other by seals or gaskets, each substrate supporting a mesh, grid or permeable membrane that incorporates a suitable sorbent material, through which sample may flow axially.

DETAILED DESCRIPTION

A detailed description of preferred exemplary embodiments of the invention is provided with reference to FIGS. 5 to 14. It will be understood that these embodiments are provided to assist in an understanding of the teaching of the invention and is not intended to limit the scope of the invention to the specifics of the features described herein. Furthermore it will be understood that where elements or features are described with reference to any one specific embodiment or Figure that these could be interchanged with or replaced by those of other embodiments or Figures without departing from the scope of the claimed invention.

Figure 1:
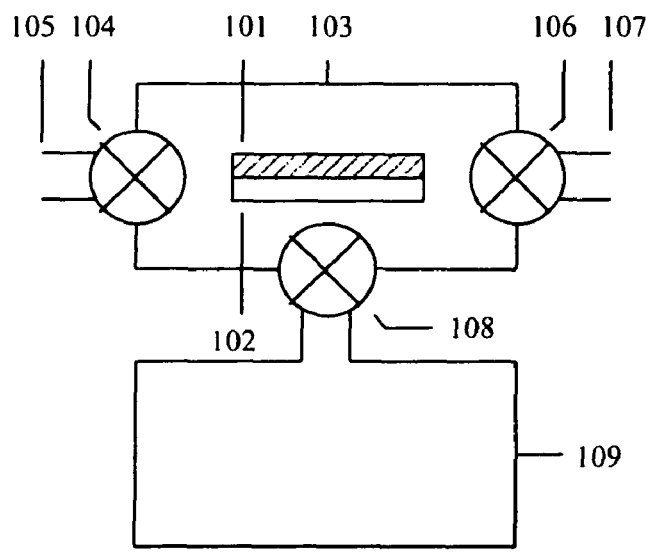
FIG. 1 shows the elements of a chemical pre-concentrator, as described in prior art.
Figure 2:
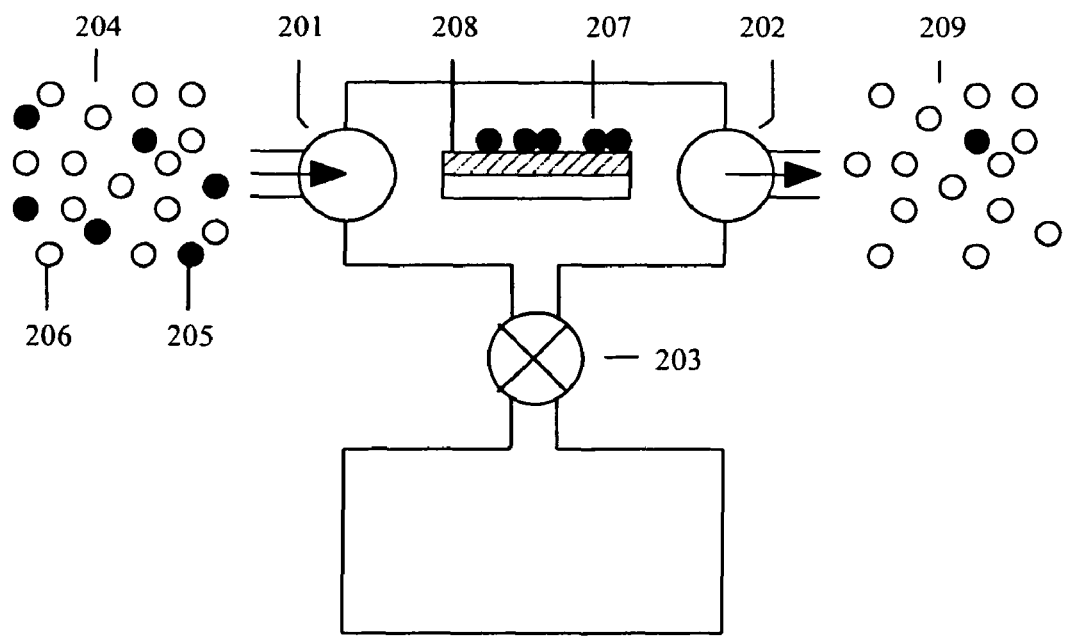
FIG. 2 shows the sorption step of chemical pre-concentration, as described in prior art.
Figure 5:
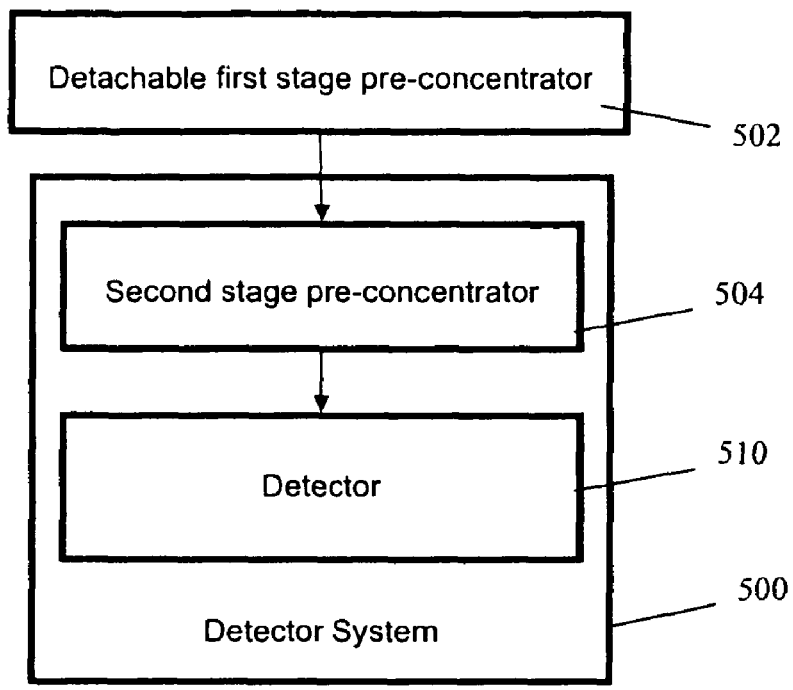
FIG. 5 is a schematic showing a multi-stage pre-concentrator system wherein the first stage is detachable in accordance with the teaching of the invention.

FIG. 5 describes a detection system 500 with a multi-stage pre-concentrator, wherein the first stage 502 is detachable. The detachable pre-concentrator may be hand portable, and may be used to gather sample remotely from the detection system. The detachable pre-concentrator may be a relatively simple, lightweight and cheap assembly manufactured using COTS and if for example used in military environments may be carried on a soldiers clothing, body armour, webbing or helmet. After the sample has been collected, the detachable pre-concentrator device may be reinserted into, and reattached onto, the detection system 500, coupling it with the second stage pre-concentrator 504. The detachable pre-concentrator may then be electrically connected to the detection system to heat its sorbent material, desorbing analyte of interest for further concentration inside the second stage pre-concentrator. The first stage pre-concentrator collects the species of interest which is sorbed into some chemically selective material. The sorbent material is then subsequently heated to release the analyte species in a relatively pure state, which may be drawn into the second stage. The second stage pre-concentrator further sorbs, concentrates and releases an even purer 'slug' of the analyte into the detector 510. The detector analyses and identifies the analyte based on some unique chemical signature (e.g. ion mobility, molecular weight, molecular fragmentation, fluorescence, thermal conductivity etc.), the specifics of which will, as will be understood by those skilled in the art, depend on the specifics of the detector system used. As the second stage is operable as a trap it desirably requires at least three valves. As mentioned above, the second stage further concentrates the sample before releasing it into a suitable detector for analysis. The detachable pre-concentrator may be removed once it has transferred the collected sample to the second stage, at which point another detachable pre-concentrator device may be inserted and attached, and the cycle is repeated. In this way one detection system could quickly analyse the contents of several detachable pre-concentrator devices carried by several users during operational duties, searches of vehicles and building and so on.

Figure 6:
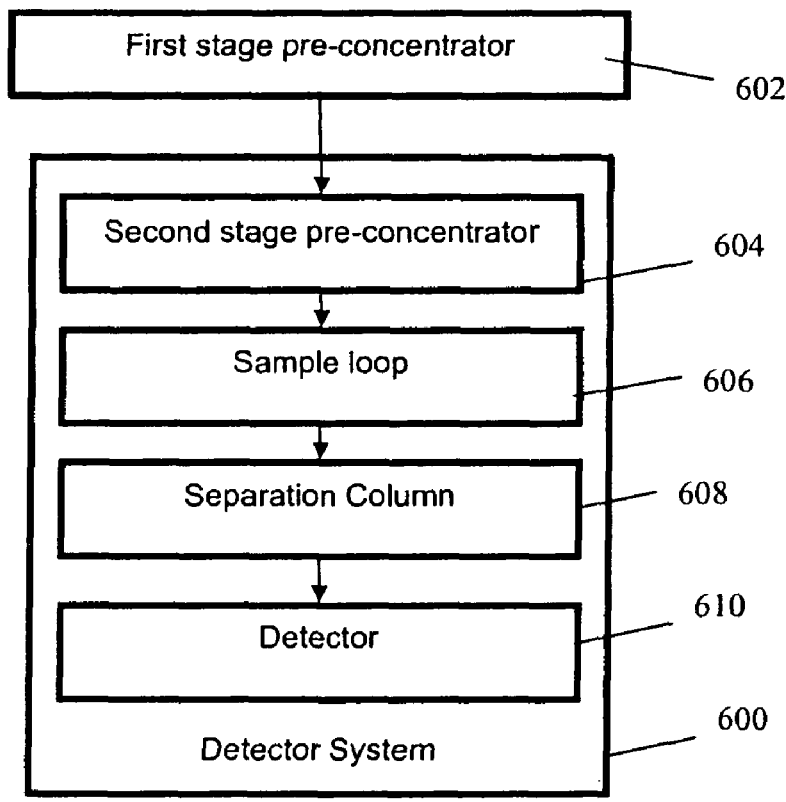
FIG. 6 is a schematic showing a multi-stage pre-concentrator coupled with a sample injection loop for a chromatography column and detector.

FIG. 6 shows a detection system 600 with a multi-stage pre-concentration system. The first stage 602 of the pre-concentrator system is detachable from the second stage 604 as before, and may be reattached once a sample has been collected remotely. The second stage pre-concentrator interfaces with a sample loop 606 of fixed volume. Sample loops are commonly found in Gas Chromatography (GC) and Liquid Chromatography (LC) systems. The sample loop serves to measure out and contain a fixed volume of analyte prior to injection into a chromatography column 608 for separation and analysis by a detector 610. A fixed volume of analyte may be injected into the column by introducing a purge gas, carrier fluid or eluent into the sample loop, which pushes a known volume of sample into the chromatography column. Sample loops and valves, however, can introduce dead volume, diluting the concentrated sample from the second stage pre-concentrator and reducing the sensitivity of the detection system.

Figure 7:
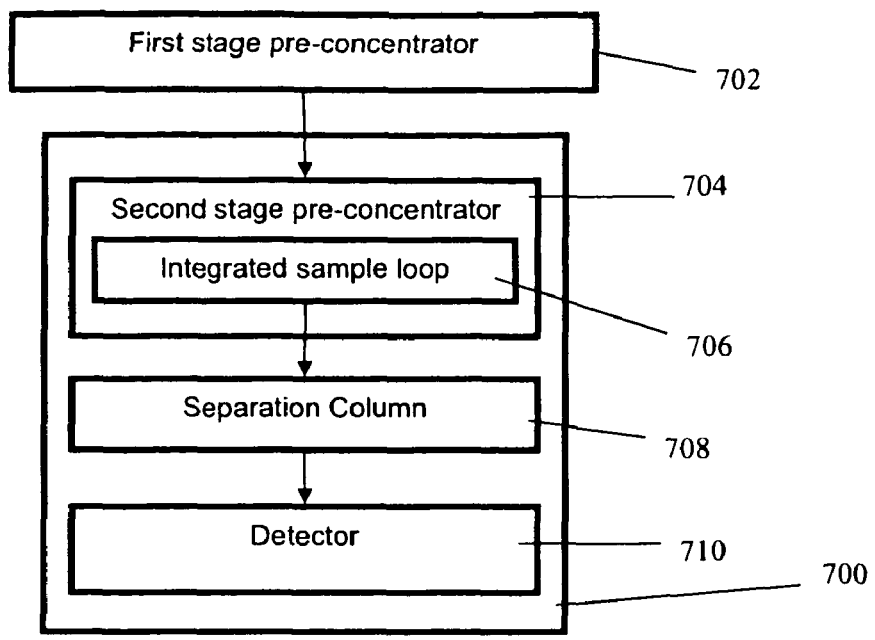
FIG. 7 is a schematic of a detector system featuring a multi-stage pre-concentrator wherein the first stage pre-concentrator is detachable and the second stage integrates a sample injection loop, and which is coupled to a chromatography column and detector.

FIG. 7 shows the same detection system 700 as in FIG. 6, having a first stage pre-concentrator 702, a second stage pre-concentrator 704, separation column 708 and a detector 710, with the important difference that the second stage pre-concentrator 704 incorporates a sample injection loop 706. The aim of integrating the sample loop with the second stage pre-concentrator is to eliminate dead volumes and cold spots normally introduced by the addition of a sample loop. In this way the large concentration factor arising from the multi-stage pre-concentrator is maintained.

Figure 8:
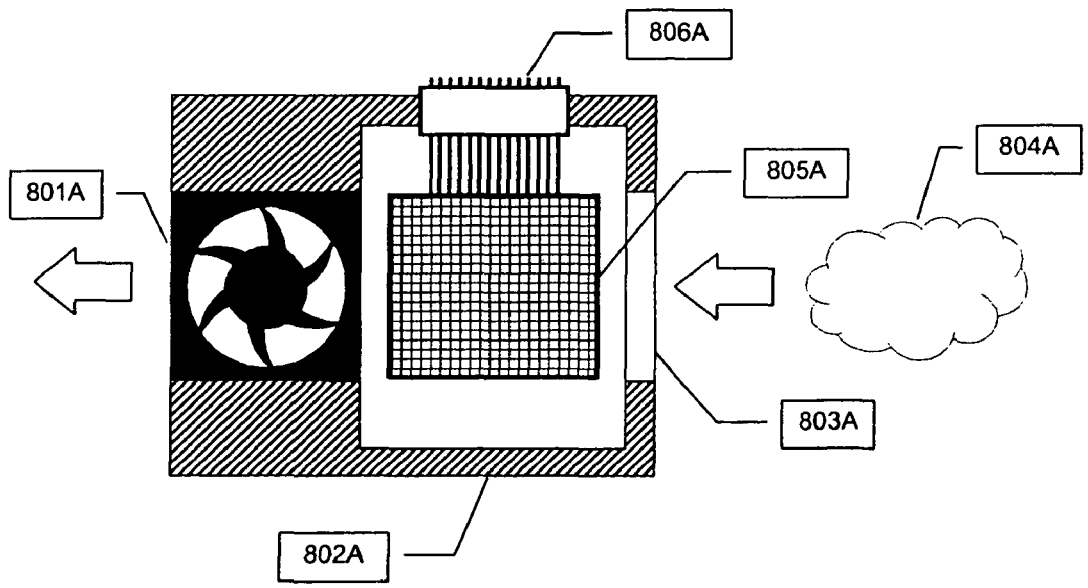
FIG. 8($a$) is a diagram of a detachable pre-concentration device.
Figure 8:
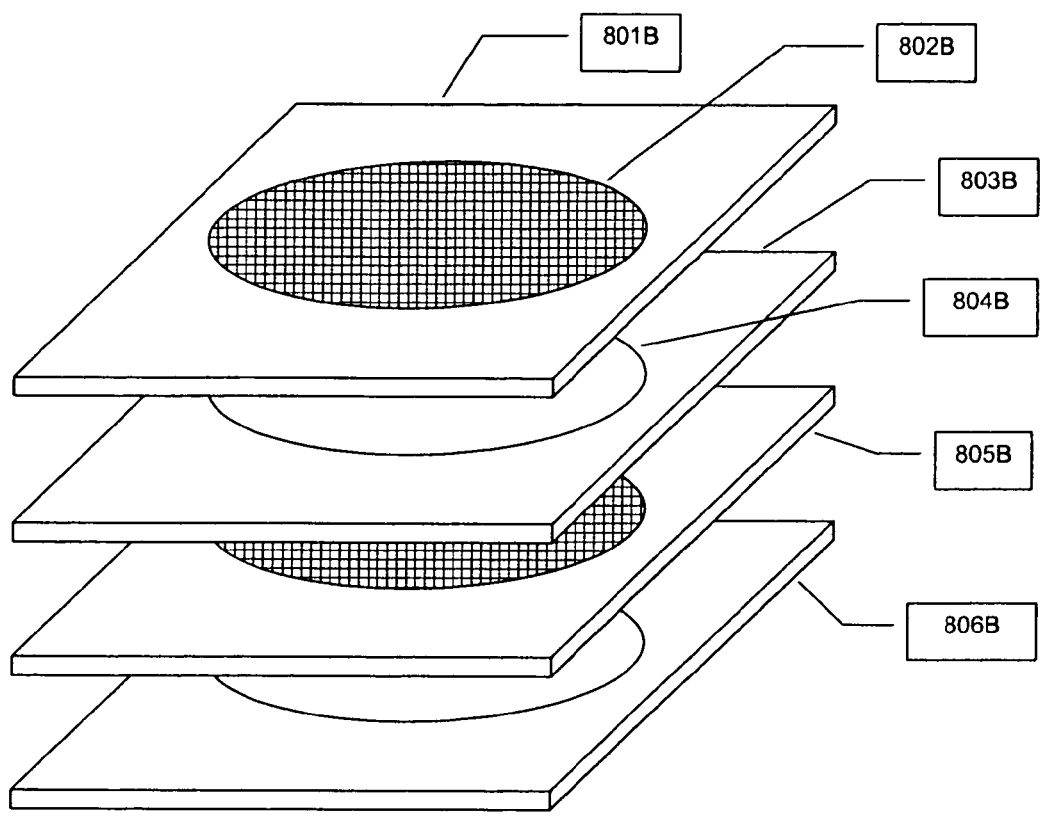
Figure 8:
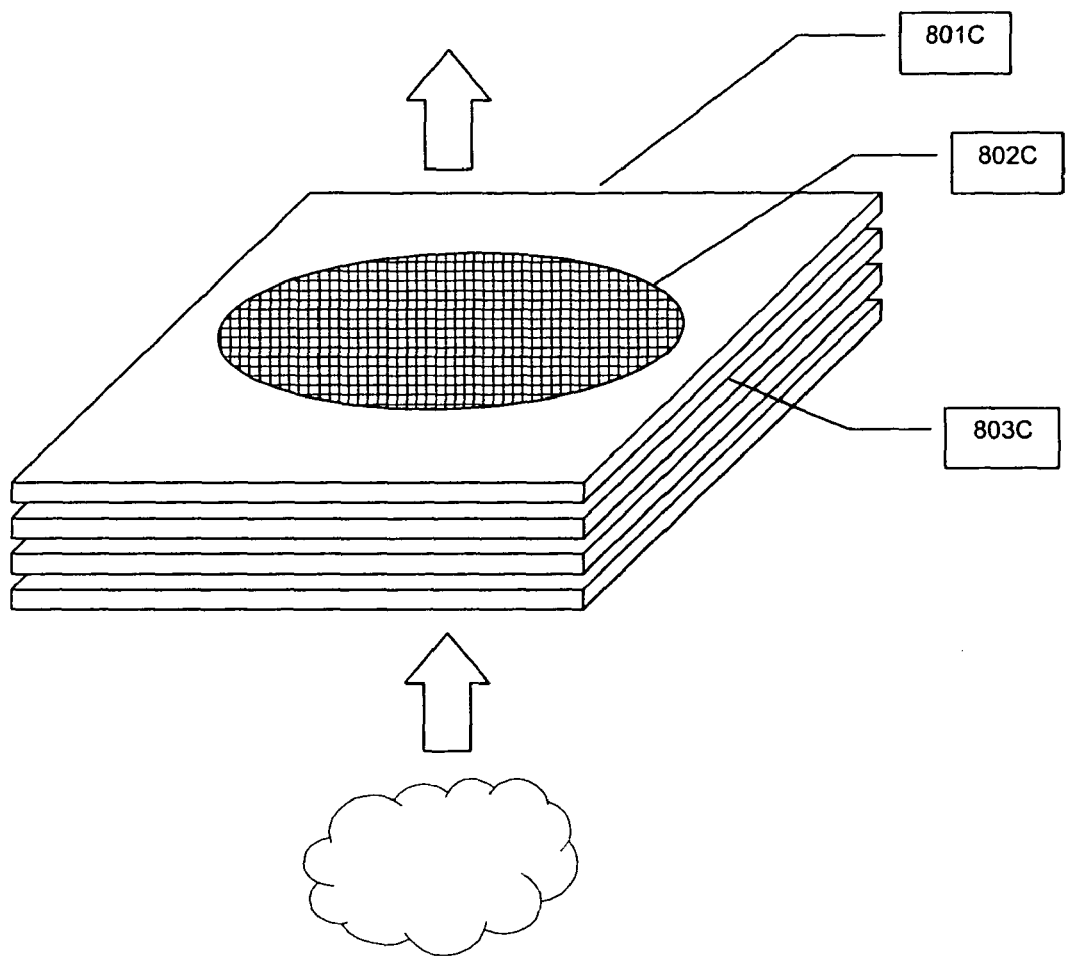
Figure 9:
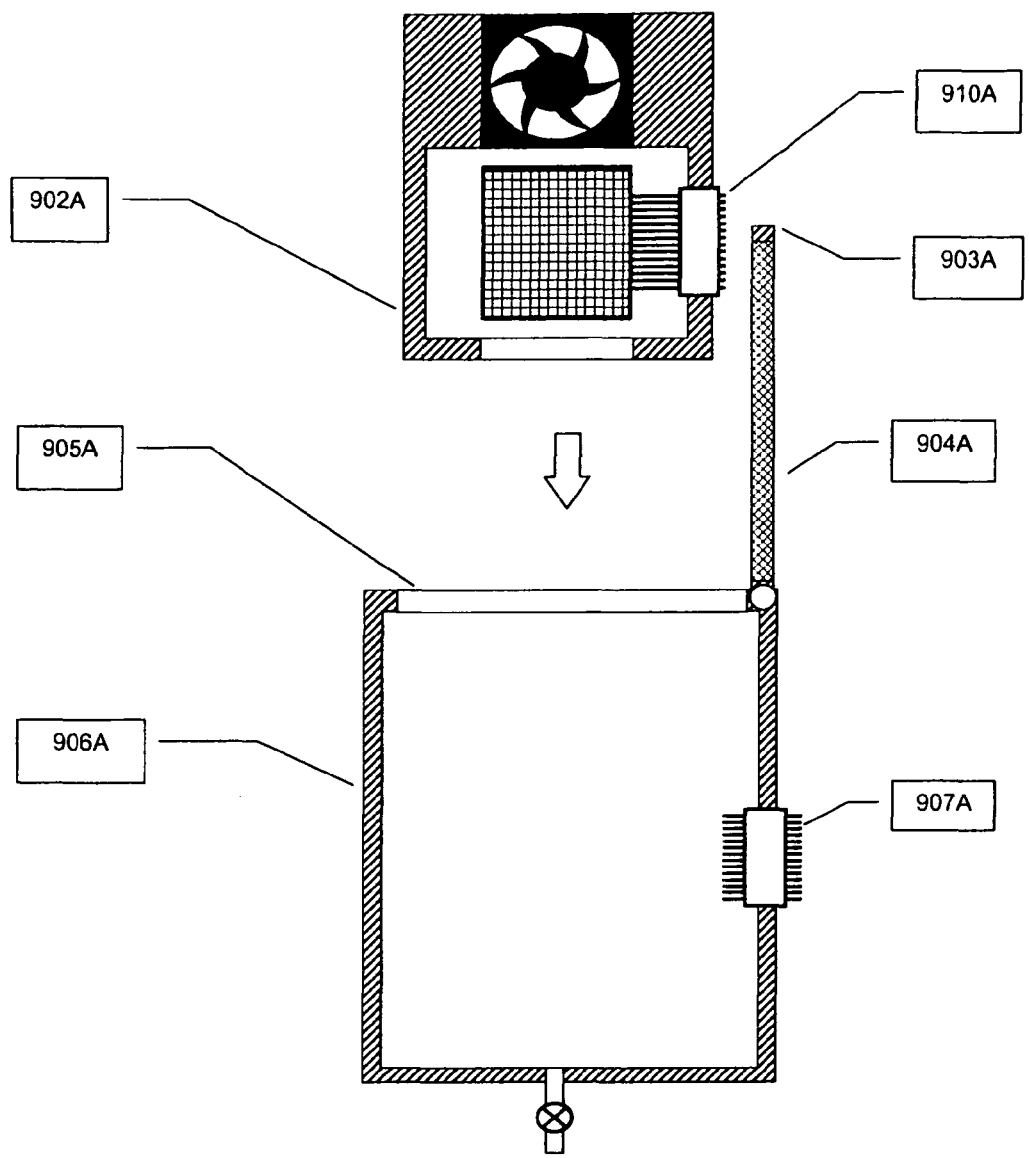
FIGS. 9($a$) and ($b$) show a detachable pre-concentrator device inserting into, and mounted inside, an interface to a detector system respectively.
Figure 9:
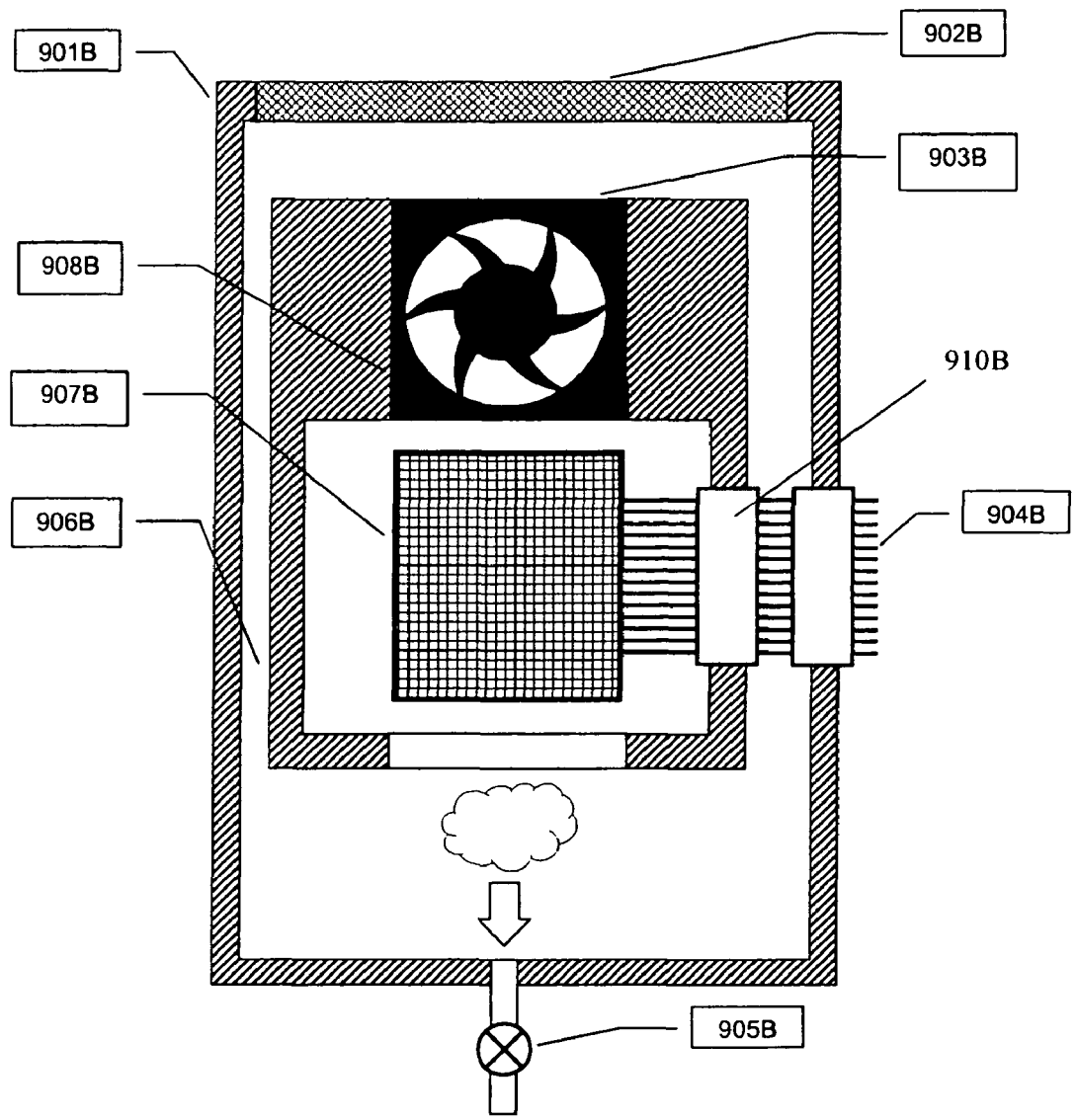
Figure 10:
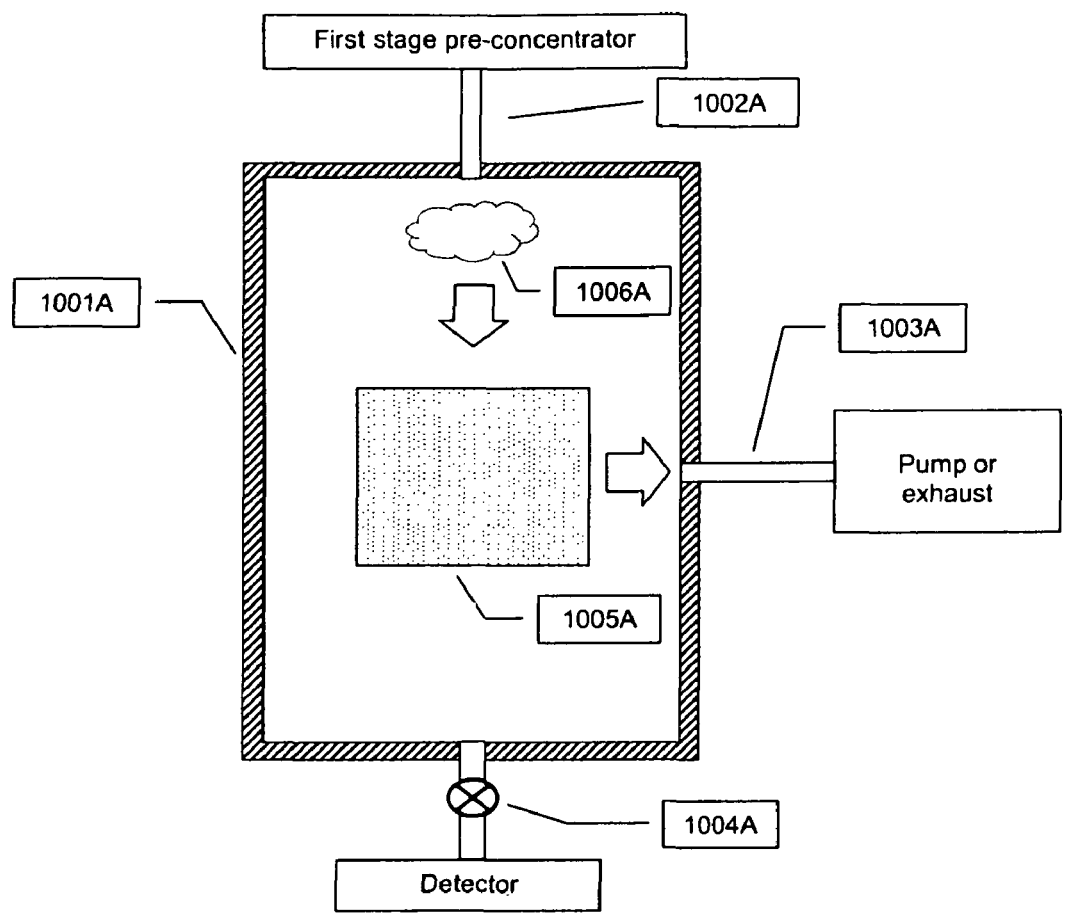
FIGS. 10($a$) and ($b$) shows one mode of operation of the second stage of a multi-stage pre-concentrator system.
Figure 10:
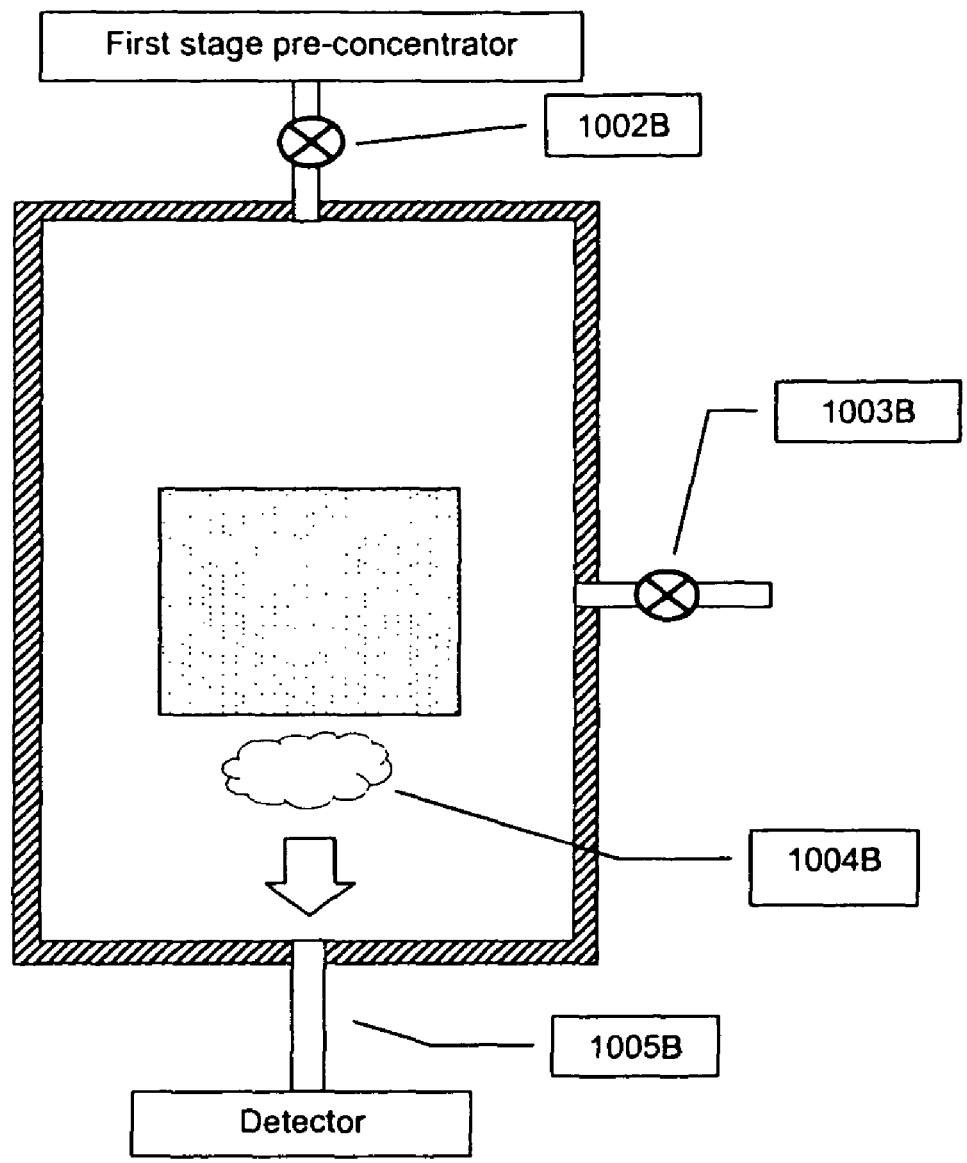
Figure 11:
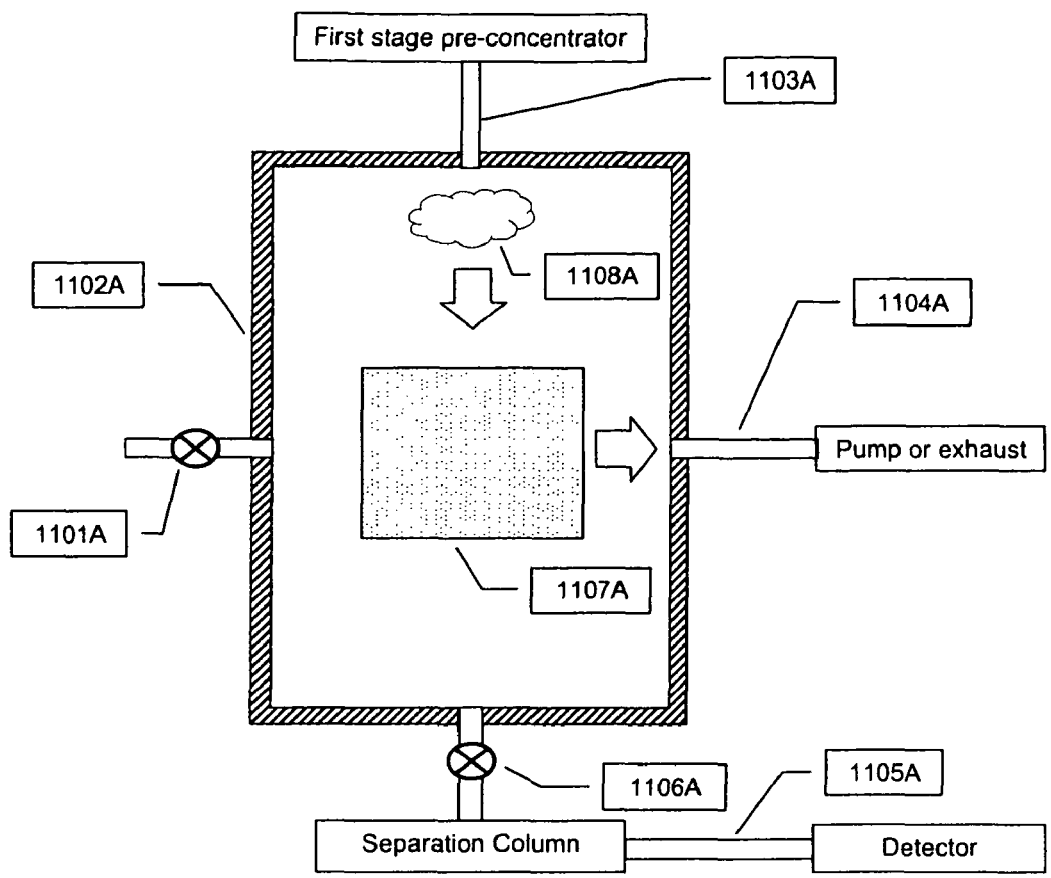
FIGS. 11($a$), ($b$) and ($c$) shows another mode of operation of the second stage of a multi-stage pre-concentrator system, wherein the second stage also serves as the sample loop of a chromatography column.
Figure 11:
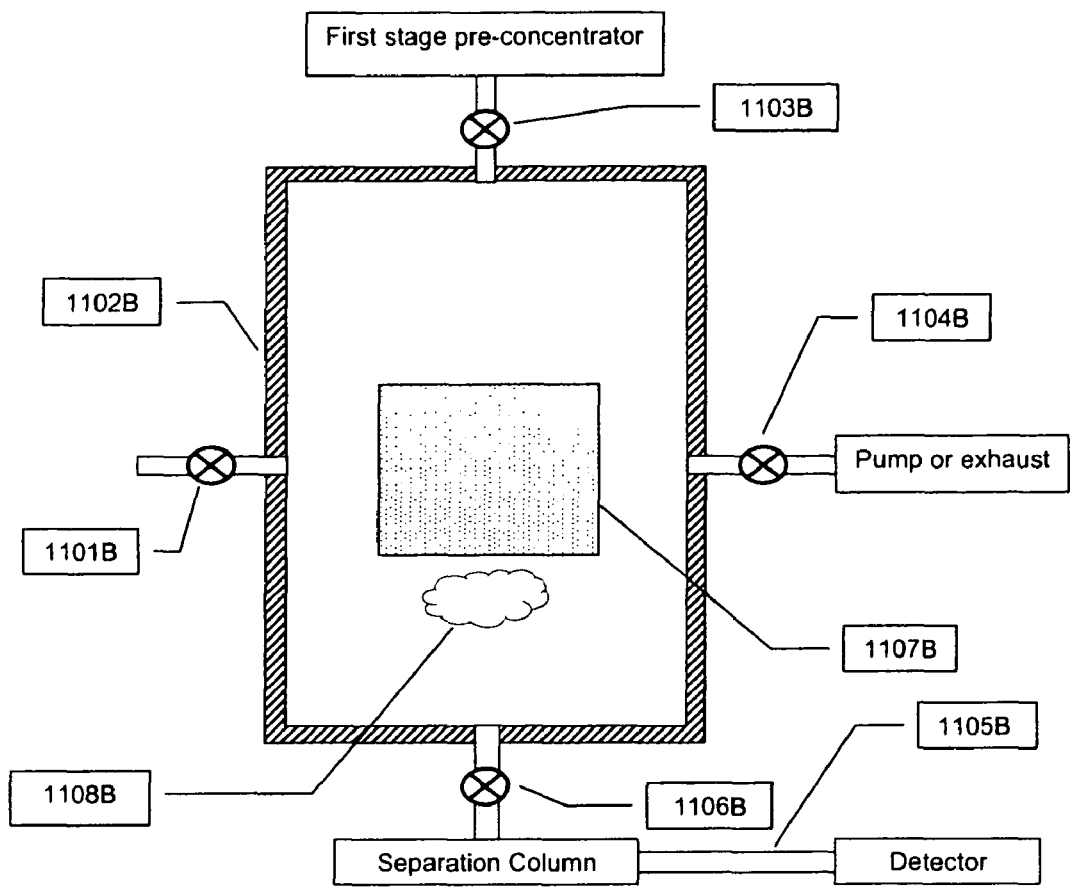
Figure 11:
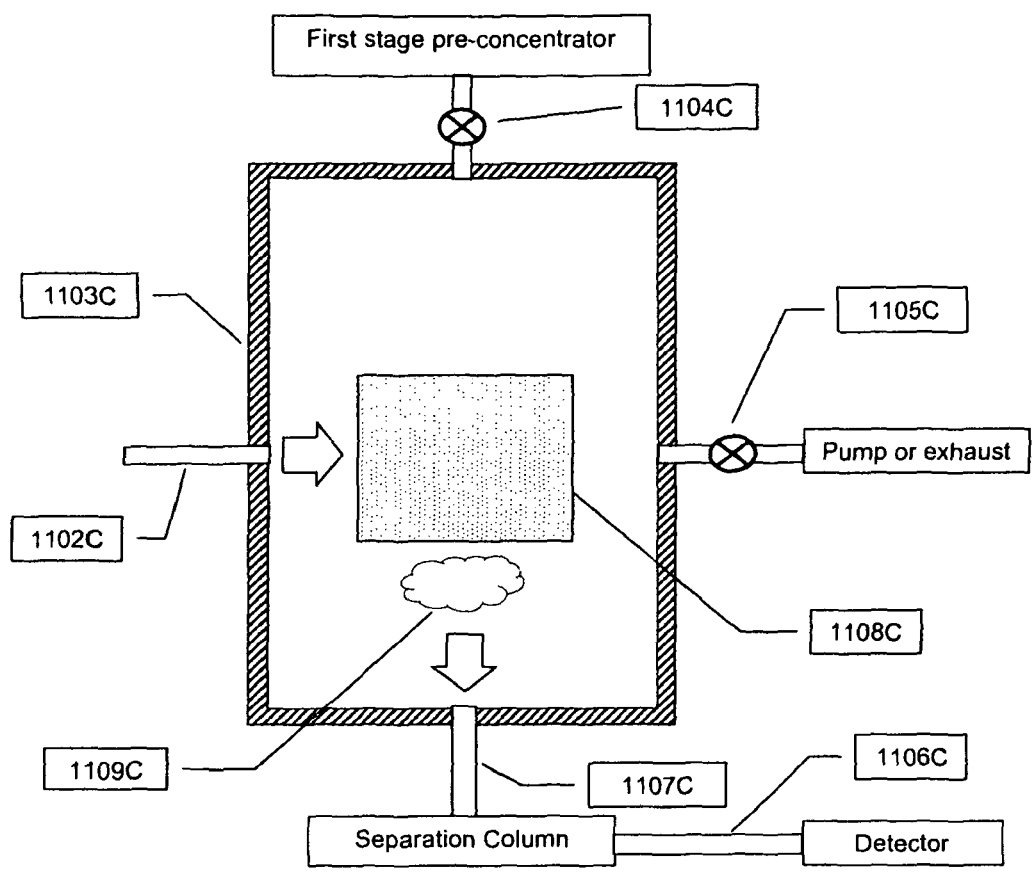
Figure 12:
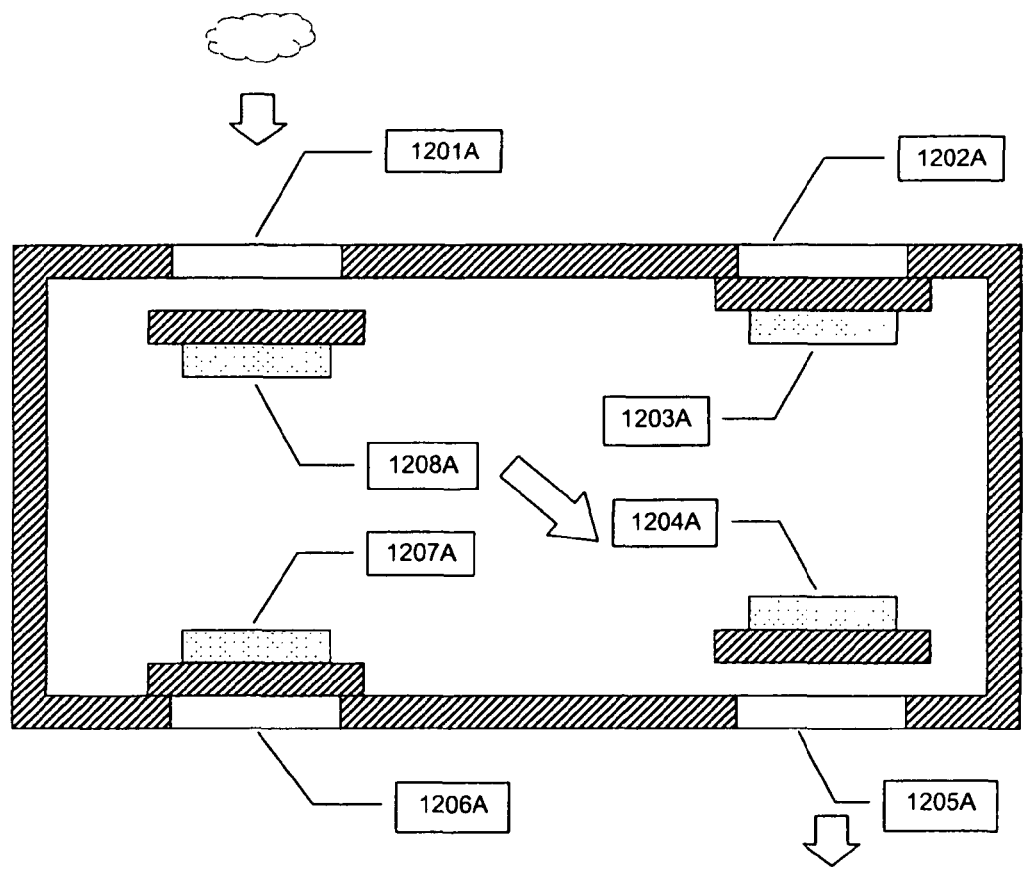
FIGS. 12($a$), ($b$) and ($c$) show the operation of a second stage pre-concentrator device wherein the valves are integrated with sorbing material.
Figure 12:
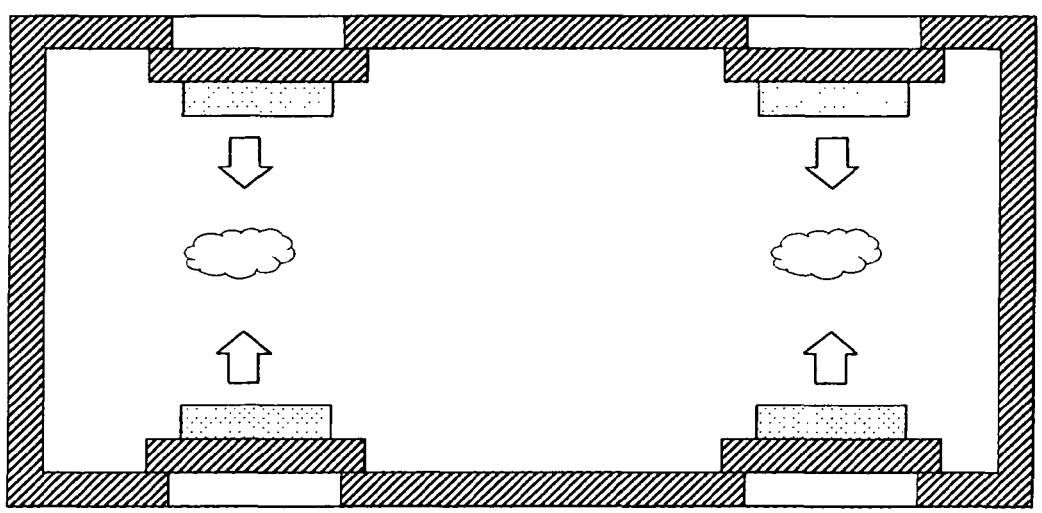
Figure 12:
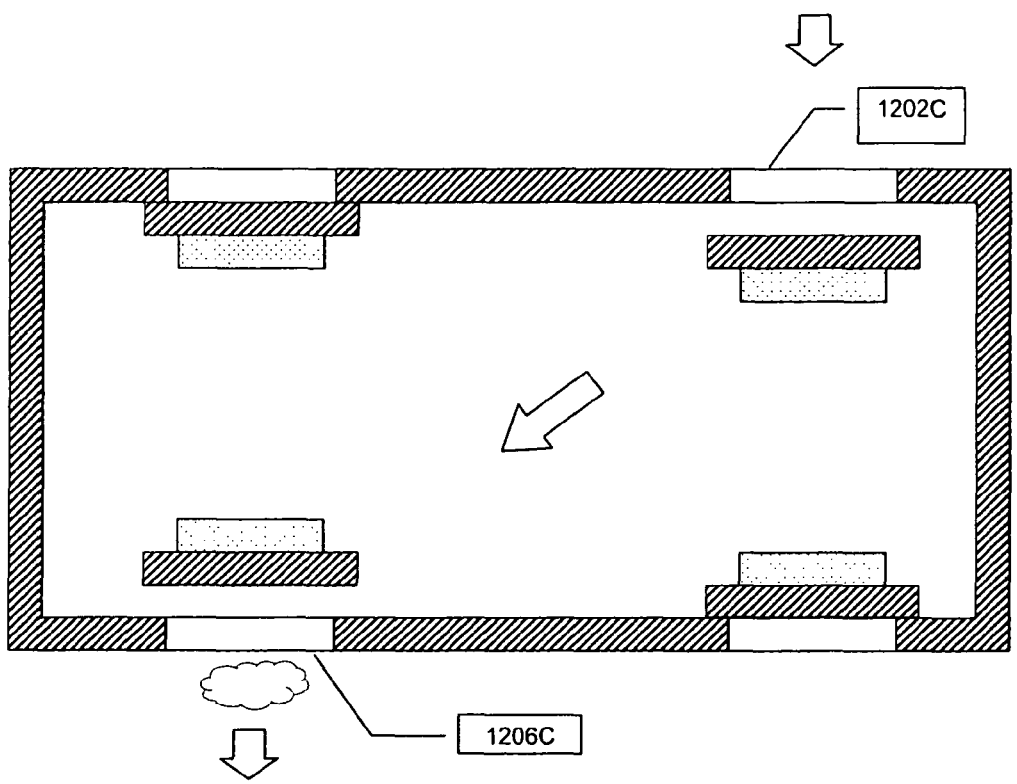
Figure 13:
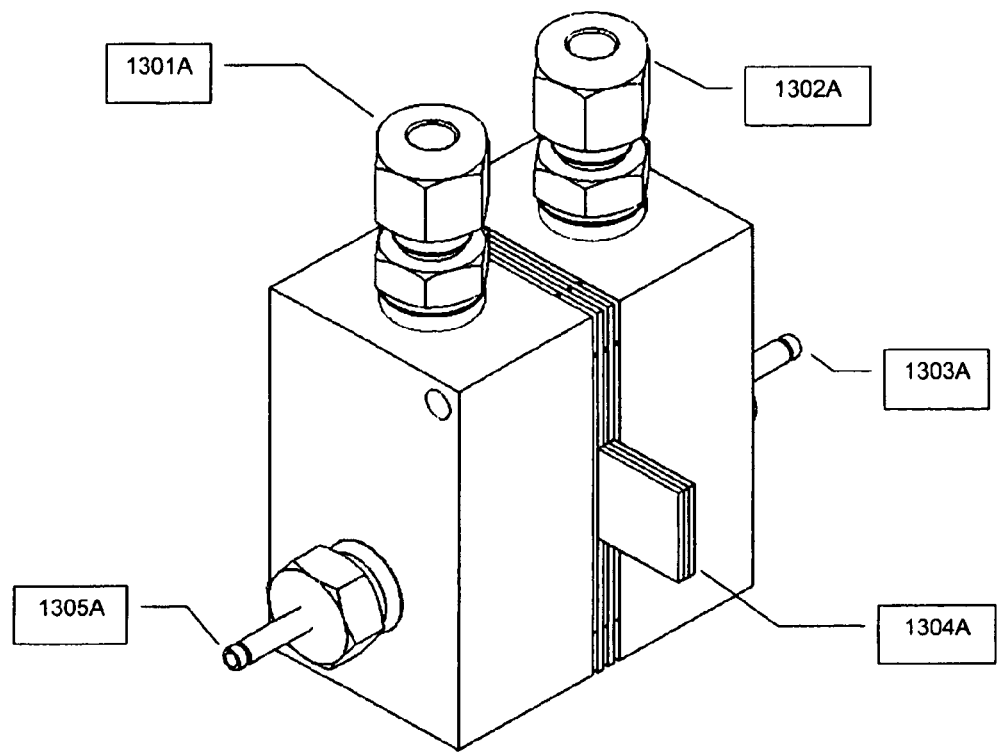
FIGS. 13($a$) and ($b$) show assembly and exploded views respectively of a device incorporating a pre-concentrator device that makes use of valves integrated with sorbent materials.
Figure 13:
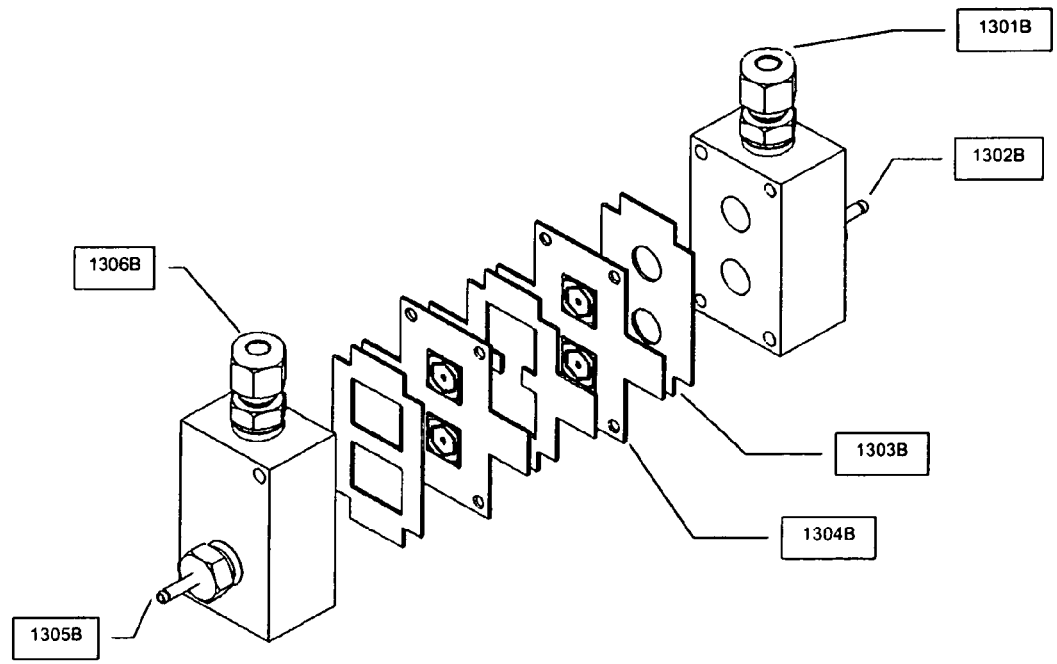

FIG. 8(a) is a schematic of a detachable pre-concentration device that may be provided in accordance with the teaching of the invention. A fan or pump 801A may be provided to deliver a controlled flow of fluid through the device. As will be understood from the following description the fan or pump where provided assists during both the sorbent and desorbent steps. During the sorbent step, it provides for a pulling of a sample flow over the sorbent material whereas during the desorbent step it achieves a pushing of the emitted sample from the first stage pre-concentrator and into the second stage pre-concentrator. As shown in FIG. 8, a fan or pump 801A may be included in an enclosure 802A to draw sample 804A into the device in the direction of the arrows and through an inlet 803A. An alternative embodiment does not provide a fan or pump, and ambient air flow is used to flow sample through the device. The device may be sealed, normally in the closed state over inlet 803A, to preserve the integrity of the sorbent membrane 805A, prevent contamination during storage or to protect from dust. The seal is in the open state when the device 802A is in use.

As was mentioned above, the sorbent mesh 805A may be sealable through some form of breakable seal, be that of the form that is resealable for example a valve arrangement, or a permanently breakable seal such as that provided by a rupturable membrane. The provision of a sealable enclosure can serve to ensure that the mesh is not contaminated during periods of non-use. In an alternative arrangement the first stage can be provided in a separate casing where it may be stored during periods of non-use.

The fan, where provided, may be located upstream of the sorbent material so as to provide for a pulling of a fluid past the mesh during the sorption cycle, and to assist in an expulsion of a collected sample out of the mesh during desorption. The mesh 805 may be a permeable membrane, matrix, mesh or lattice made from some suitable chemically selective material, metal, semiconductor, polymer, conductive composite or coating to sorb the species of interest from the impure sample stream delivered by 801A. Suitable materials may be selected for a species of interest (e.g. chemical weapons, toxic industrial chemicals, explosives, biological weapons, process gases etc).

Once a sample has been collected, the detachable pre-concentrator device may be returned to, and inserted into, a detector system and connected via an electrical interconnector 806A. To desorb the sample, the mesh 805A may be resistively heated by applying a current via an electrical interconnector 806A. It will be understood that heating is not essential but does represent a conventional way to desorb from a sorbent material—other ways include using a liquid to wash out the species of interest e.g. SPME sample probes use PDMS fibres to sorb sample and can be dipped into an aqueous stream to desorb them, or inserted into a heated region like a heated sample port. The enclosure 802A may also include a suitable power supply such as batteries to drive the pump or fan 801A when in use remotely from the detector system. Desirably if provided these batteries are rechargeable and may be recharged during the periods when the detachable first pre-concentrator device interfaces with the detection system, the detector system supplying power via an electrical interconnect 806A.

FIG. 9(a) shows an example of how a detachable sample collection device 902A may be inserted into an interface housing 906A to mount the collection device 902A inside a detector system. A receiving portion corresponding in dimension to the external dimensions of the first pre-concentrator is provided within the interface housing. A lid 903A and incorporating a fine dust filter 904A is provided, which on opening allows presentation of the first stage into the interface housing. The lid 903a may be hinged. Once inserted, the housing lid 903A may be closed to encapsulate the first stage within the interface housing 906A. If the desorption step utilises an air flow, it will require a flow past the mesh of the first stage and in this way it is desirable that the interface housing include some means to allow generation of the requisite air flow. In this exemplary arrangement an aperture—sealed against dust by the provision of the dust filter 904A is provided in the lid. It will be understood however that the actual location of the aperture and corresponding dust filter is not critical, and the two could be located elsewhere in the housing.

One embodiment of sorbent mesh 805A is shown as an exploded view in FIG. 8(b). The sorbent mesh is formed from a stack of PCBs represented by 801B and 805B, interleaved with gaskets or seals represented by 803B and 806B. The seals or gaskets 803B and 806B each have holes 804B through which a gas stream may pass in an axial direction and hence through the mesh, permeable membrane, lattice, grid or matrix 802B without leaking. Each PCB may have through-holes, vias, or a cut-out drilled through it, forming a hole or set of holes 802B over which a suitable chemically sorbent material such as PDMS, may be deposited.

In FIG. 8(c) the stack is shown as an assembled stack of PCBs represented by 801C, and gaskets shown as 803C, through which a gas stream containing a species of interest flows axially through a series of meshes, comprising a sorbent material shown as 802C. In FIG. 8(c) the sample is sorbed as it passes through the stack, which provides the sorbent mesh 805A. It will be understood that the stack is provided transverse to the direction of the sample flow so as to maximise the contacted area of sorbent material to the sample flow.

FIG. 9(a) shows how a detachable sample collection device 902A may be inserted into an interface housing 906A to mate the collection device 902A inside a detector system. A lid 901A, which in one embodiment incorporates a fine dust filter 904A, is provided and serves to protect the second stage from dust which could clog orifices, seals and valves. If the desorption step utilises a liquid, such a dust filter may not be required. As mentioned above, movement of the lid enables an insertion of the sample collection device 902A through opening 905A and into housing 906A. The sample collection device has an interconnect 910A which may be used to securely attach it to a receiver 907A, thereby effecting physical and electrical contact with the detector system. Lid 903A may then be closed, sealing collector 902A inside the interface housing. It is also possible that the housing of the first stage 902A could provide the necessary lid to the interface housing such that the insertion of the first stage closes the opening 905A, thus obviating the need for a separate lid.

FIG. 9(b) is a diagram of a detachable pre-concentrator device 902A mounted inside an interface 901B to a detector system. In one embodiment, the interface may be an enclosure 901B with a lid incorporating a dust filter 902B. The detachable pre-concentrator 902A, as described in FIG. 8(a), is inserted into the box 906B and attached to the detector system by means of coupling interconnector 910B with a second interconnector 904B mounted on the inside of the interface. Once mounted inside the interface, the lid 903A may be closed on the enclosure 901B. To rapidly desorb the sample collected by the detachable pre-concentrator 902A, the sorbent mesh 907B may be electrically heated. The sample may then be driven into the second-stage pre-concentrator by means of fan or pump 903B. The valve 905B is opened and the fan or pump 903B may be operated in reverse to drive the desorbed analyte through valve 905B into the second-stage pre-concentrator. A dust filter 902B prevents dust particles from being drawn into the interface region 906B by the fan 908B and onto the second-stage pre-concentrator. The dust filter 902B is useful for successful operation of the second-stage pre-concentrator, in particular to operation of the valve 905B. Alternatively, a fan or pump and the dust filter 902B may be provided as part of the lid of the interface housing, or of the interface 901B.

While the coupling of the first stage to the interface housing has been heretofore described with reference to a simple insertion of the first stage into a receiving portion and the subsequent mating of the interconnectors, it will be understood that one or more guides may be provided to facilitate the accurate alignment and coupling of the first stage to the detector system.

FIGS. 10(a) and (b) shows a mode of operation of the second stage of a multi-stage pre-concentrator system. In FIG. 10(a) the species of interest 1006A desorbed from the first stage pre-concentrator is in a relatively pure state and is drawn into the second-stage pre-concentrator 1001A via inlet 1002A by means of the fan or pump 908B, and/or (if a negative pressure inside 1001A is desired) by means of a pump connected to port 1003A. Alternatively port 1003A may be simply an exhaust or vent to the ambient air. A third valve 1004A between the second-stage and a detector is normally in the closed position during the trapping cycle. In this way a relatively pure stream of analyte species 1006A desorbed from the first-stage pre-concentrator passes over a suitable chemically selective, sorbent material 1005A. In FIG. 10(b) valves 1002B and 1003B are in the closed position. The sorbent material 1005A is heated to desorb a pure 'slug' of analyte 1004B, which is drawn into the detector via port 1005B, with valve 1004A now in the open position (valves not shown in FIG. 10(b) for simplicity of illustration) during the desorbing cycle. The detector connected to outlet port 1005B may be a mass spectrometer, ion mobility spectrometer, flame ionisation detector, surface acoustic wave (SAW) detector, thermal conductivity detector, electrometer, chemical fluorescence detector or some other reliable means of 'fingerprinting' the chemical composition of analyte species 1004B.

FIGS. 11(a), (b) and (c) shows another mode of operation of the second-stage of a multi-stage pre-concentrator system, wherein the second stage also serves as the sample loop or injection volume of a separation column. The advantage of integrating the sample loop with the pre-concentrator is reduced dead volume, minimising re-dilution of the desorbed analyte, and permitting greater loading of the column in less time. This will mean that the detector system will enjoy greater sensitivity, faster response time and a reduced duty cycle. In FIG. 11(a), a relatively pure stream of the species or analyte of interest 1108A is desorbed from the first-stage and drawn down inlet port 1103A into the second-stage device 1102A by means of positive pressure in the first-stage, and/or a negative pressure inside the second-stage trap induced by a pump connected to port 1104A. During the trapping cycle the analyte stream 1108A passes over a suitable chemically selective material 1107A, which may be a sorbent metal such as titanium or a suitable sorbent polymer such as Tenax or PDMS, or some suitable composite material. During the trapping cycle a third valve 1101A, connecting the second-stage 1102A to a reservoir containing a mobile phase, and a fourth valve 1106A connecting 1102A to a separation column, are in the closed position. In FIG. 11(b) the trapping cycle is complete, and all four valves 1101B, 1103B, 1104B and 1106B are in the closed position. The sorbent material 1107B is heated, desorbing a highly concentrated 'slug' of analyte 1108B which fills the small trapping volume 1102B. Alternatively, desorption may be carried out with valves 1101B and 1106B open.

In FIG. 11(c) valves 1104C and 1105C are still in the closed position, but ports 1102C and 1107C are open. Inlet port 1102C is connected to a reservoir containing a mobile phase, carrier gas or eluent. Carrier gases and mobile phases are typically gases or solvents and are used by analytical instruments like GC systems, LC systems, Supercritical Fluid Chromatography (SFC) and ion mobility spectrometers to transport sample through separation columns and into detectors. The second-stage pre-concentrator trapping volume 1103C is now filled with a pure volume of species of interest 1109C, and with ports 1102C and 1107C open, mobile phase, carrier gas or eluent enters 1103C through port 1102C and pushes a defined volume of analyte species 1109C from the trap and into the column via port 1107C. In this way, the trapping volume acts a pre-concentrator and as a sample loop of defined injection volume, minimising dead volume. Analyte species 1109C is separated by the column, and eluted into the detector via port 1106C.

A preferred embodiment of a second-stage pre-concentrator device that also serves as a sample loop is described in FIGS. 12(a), (b) and (c). FIG. 12(a) shows the operation of a second-stage pre-concentrator device wherein the valves and sorbent materials are integrated into the same structure. Such a pre-concentration device may be preferably as described in GB 2434643A. In FIG. 12(a), the analyte stream enters the device through port 1201A, which may be connected to a first-stage, or some other stage, pre-concentrator device. In FIG. 12(a) valves 1208A and 1204A are both in the open position. Valves 1208A and 1204A both support a layer, coating or structure fabricated from some suitable chemically selective, sorbent material such as Tenax or PDMS. Alternatively this material may be fabricated from a suitable chemically sorbent surface such as titanium, or based on a textured absorbing layer formed from carbon nanotubes, suitably coated microstructures or some suitable composite material. Port 1205A is also open and may be connected to either an exhaust port or to a pump if a negative pressure is desired inside the trapping volume in order to draw in the analyte stream from the first-stage pre-concentrator. In this way, the sample flows in through port 1201A and over the sorbent materials on 1208A, 1203A, 1207A and 1204A before venting through 1205A. Some or all of these valves may support a sorbent material. Analyte species are collected by the sorbent material inside the trap.

In FIG. 12(b), all the ports are closed and the valves may be heated to desorb analyte into the trapping volume. The trap is now filled with pure species of interest and serves as a sample loop of a known, fixed injection volume.

In FIG. 12(c) valves 1203A and 1207A are in the open position, and a mobile phase or carrier gas may flow in through port 1202C from a reservoir. The mobile phase or carrier fluid 'pushes' a defined volume of concentrated analyte out of the trap and through 1206C, which may be connected to a column. In this fashion the trap serves as a sample loop for rapidly injecting a high concentration 'slug' of known volume into a chromatography column for separation and analysis. By integrating the valves and sorbing materials, a minimal dead volume is realised, preventing further dilution of the analyte species prior to injection into the separation column through 1206C.

Equally, instead of a carrier gas, the pre-concentrator device could be coupled via port 1202C to a reservoir of mobile phase which is a liquid. This liquid could be a typical solvent or eluent which can dissolve the species of interest while not being retained by the sorbent material in the trap. In this alternative embodiment, the trapping cycle may be the same as illustrated in 12(a) and (b), but in 12(c) a liquid enters the trap through 1202C and purges the analyte out, effectively washing the analyte from the sorbent material and into a liquid stream connected to 1206C. This liquid may then be separated in a LC system and analysed in a downstream detector, or directly ionised in a detector which may be a mass spectrometer with means of ionising liquids such as Electrospray Ionisation Mass Spectrometry (ESI-MS), or some other suitable Atmospheric Pressure Interface (API) that ionises the liquid stream and couples it into a mass spectrometer detector. In this way the trap serves as a pre-concentrator and as a sample injection loop of known volume for a liquid chromatography mass spectrometer system (LC-MS), or for an electrospray ionisation mass spectrometer system (ESI-MS).

FIGS. 13(a) and (b) are assembly and exploded views of an embodiment of the second stage pre-concentrator device which features valves integrating sorbent material. Port 1301A couples with the housing or receiver for the first-stage pre-concentrator, port 1305A couples with the reservoir for the mobile phase or carrier gas, port 1303A couples with the detector, and port 1302A couples with the exhaust or pump. In the figure, 1304A represents a stack of PCBs and gaskets, incorporating the integrated valve and sorbent material microstructures. In FIG. 13(b), the exploded view shows ports 1306B, 1301B, 1302B and 1305B that correspond to the ports in 13(a). The printed circuit boards (PCBs) supporting the integrated valve and sorbent material are represented by 1304B, and the gaskets are represented by 1303B. Equally, FIG. 13(a) and (b) could describe the detachable first-stage pre-concentrator, where 1304B is a PCB supporting a sorbent mesh manufactured using conventional technology, rather than a microstructure forming an integrated valve and sorbent material.

Figure 14:
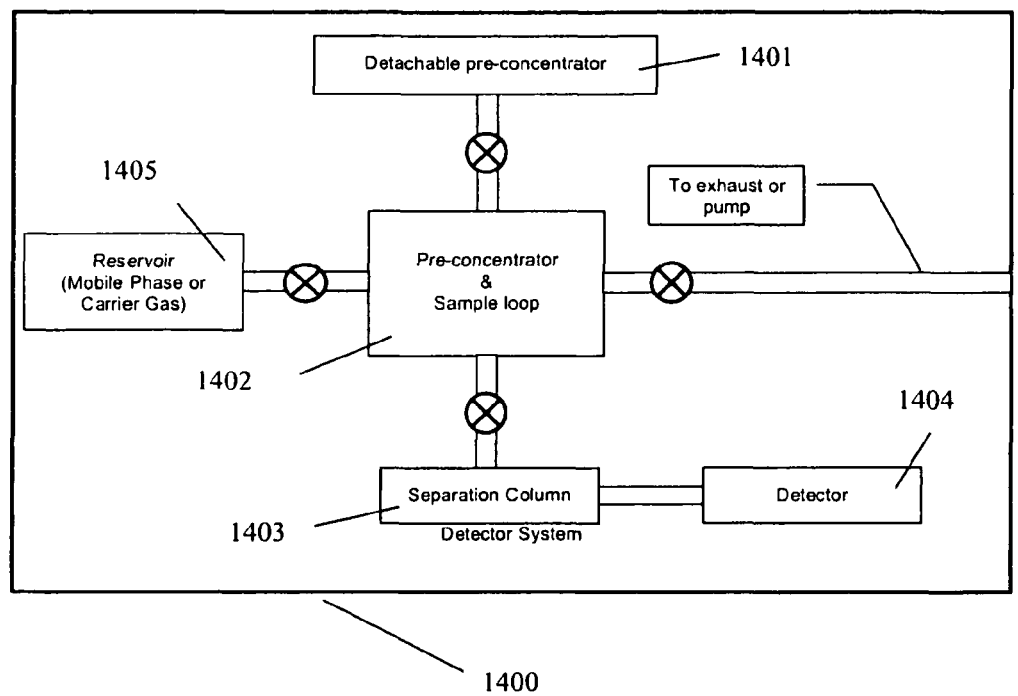
FIG. 14 is a schematic describing a detection system featuring a two stage pre-concentrator and chromatography column, wherein the first stage pre-concentrator is detachable, and the second stage pre-concentrator device also serves as a sample loop for the chromatography column.

FIG. 14 is a schematic of an overall system incorporating a first-stage detachable pre-concentrator device 1401 for remote sampling, a second-stage pre-concentrator 1402 that also functions as a sample loop, a separation column 1403, detector 1404, reservoir 1405 containing a mobile phase and associated valves.

It will be understood that what has been described herein are exemplary embodiments of a multi pre-concentrator stage detector system wherein a removable first stage of the pre-concentrator is provided to assist in sampling procedure remote from the actual point of analysis. While the invention has been described with reference to preferred arrangements it will be understood that these are provided to assist in an understanding of the teaching of the invention and it is not intended to limit the invention in any way except as may be deemed necessary in the light of the appended claims.

The words comprises/comprising when used in this specification are to specify the presence of stated features, integers, steps or components but does not preclude the presence or addition of one or more other features, integers, steps, components or groups thereof.

REFERENCES

Mitra S., Yun C. "Continuous gas chromatographic monitoring of low concentration sample streams using an on-line microtrap" J. Chromatogr. A 648, 415-421 (1993)

Feng C. H., Mitra S. "Two-stage microtrap as an injection device for continuous on-line gas chromatographic monitoring" J. Chromatogr. A805, 169-176 (1998)

Mitra S. "Analytical apparatus and instrumentation for on-line measurement of volatile organic compounds in fluids" U.S. Pat. No. 6,112,602 Sep. 5, (2000)

Krishnaswamy S. V., Freidhoff C. B. "Thin film preconcentrator array" U.S. Pat. No. 5,481,110, Jan. 2 (1996)

Manginell R. P., Frye-Mason G. C. "Chemical preconcentrator" U.S. Pat. No. 6,171,378 Jan. 9. (2001)

Tian W. C., Pang S. W., Lu C. J., Zellers E. T. "Microfabricated preconcentrator-focuser for a microscale gas chromatograph" IEEE/ASME J. Microelectro-mechanical Syst. 12, 264-272 (2003)

Tian W.-C., Pang S. W., Zellers E. T. "Microelectromechanical heating apparatus and fluid preconcentrator device utilizing same" U.S. Pat. No. 6,914,220 Jul. 5 (2005)

McGill R. A., Martin M., Crain M., Walsh K., Houser E., Nguyen V. "Micro scale flow through sorbent plate collection device" US 20050095722 May 5 (2005)

What is claimed is:

1. A detector system comprising a detector coupled to a first and second pre-concentrator stage, each of the first and second pre-concentrator stages having a sorbent material to collect samples, and wherein the first pre-concentrator stage is removable from the detector so as to be portable to enable a collection of a sample within the first pre-concentrator at a location remote from the detector, and further wherein coupling of the first pre-concentrator stage to the detector defines a fluid path from the first pre-concentrator stage to the second pre-concentrator stage to the detector.

2. The system of claim 1 wherein each of the first and second pre-concentrator stages comprises means to induce a flow of a sample past the sorbent material.

3. The system of claim 2 wherein the first pre-concentrator stage includes a fan provided to assist in inducing a flow of a sample past the sorbent material.

4. The system of claim 3 wherein the fan is provided upstream of the sorbent material such that operation of the fan effects drawing of a sample flow across the sorbent material.

5. The system of claim 3 wherein the fan is operable in a first and a second mode; operation in the first mode effecting a drawing of a sample into the first pre-concentrator stage and operation in a second mode effecting a pushing of a desorbed sample out of the first pre-concentrator stage.

6. The system of claim 1 wherein the sorbent material of the first pre-concentrator stage is provided on a heatable substrate for use in effecting a desorption of a collected sample from the first pre-concentrator stage.

7. The system of any claim 1 wherein the sorbent material of the second pre-concentrator stage is provided on a heatable substrate for use in effecting a desorption of a collected sample from the second pre-concentrator stage.

8. The system of claim 1 wherein the second pre-concentrator stage is in fluid communication with a reservoir, such that a fluid from the reservoir may be operatively introduced into the second pre-concentrator stage to effect a discharge of a collected sample.

9. The system of claim 1 wherein the second pre-concentrator stage and the detector define a sample loop path therebetween, the sample loop path enabling an operative provision of a sample of a defined volume into the detector.

10. The system of claim 1 wherein the sorbent material is provided within a sealable enclosure.

11. The system of claim 10 wherein the sealable enclosure includes a re-sealable element to facilitate repeated sealing of the enclosure.

12. The system of claim 10 wherein the sealable enclosure includes a rupturable membrane which on rupturing effects a permanent opening of the enclosure.

13. The system of claim 10 wherein the first pre-concentrator stage includes a separate container within which the first pre-concentrator stage may be stored during periods of de-coupling from the system.

14. The system of claim 1 wherein the first pre-concentrator stage includes a battery.

15. The system of claim 14 wherein the battery is rechargeable.

16. The system of claim 1 wherein the system includes a housing incorporating both the detector and the second pre-concentrator stage, integrally formed as part of the housing, the first pre-concentrator stage being removable from the housing.

17. The system of claim 16 wherein each of the housing and the first pre-concentrator stage include an electrical interconnector, which on coupling of the first pre-concentrator stage to the housing mate with one another.

18. The system of claim 16 wherein the housing includes a receiving portion dimensioned to receive the first pre-concentrator stage therein.

19. The system of claim 18 wherein the receiving portion includes a moveable lid, an opening of the lid enabling an insertion of the first pre-concentrator stage into the receiving portion.

20. The system of claim 19 wherein the housing includes a dust filter, such that on closing of the lid an air path is defined through the dust filter and into the receiving portion.

21. The system of claim 1 wherein the sorbent material is selected so as to be predisposed to effect a capture of a predetermined sample species.

22. The system of claim 1 wherein at least one of the sorbent materials provided in the first or second pre-concentrator stages is provided as a multi-layer element.

23. The system of claim 22 wherein the sorbent material of the first pre-concentrator stage is provided as a multi-layer element.

24. The system of claim 22 wherein the multi-layer element includes a stack of substrates, each substrate having a sorbent material provided thereon.

25. The system of claim 24 wherein the stack is provided transverse to the direction of a sample flow past the sorbent material.

26. The system of claim 1 wherein the second pre-concentrator stage includes a trap through which a gas may flow, entry of gas into the trap through an orifice being controlled by a valve, which is moveable between a first position wherein the gas is free to move through the orifice from the first pre-concentrator stage and into the trap and a second position wherein the valve seals the orifice preventing the flow of gas into the trap, and wherein the sorbent material is provided in the trap to sorb the species present in the gas during the flow of gas through the trap.

27. The system of claim 26 wherein the valve is provided as a movable flap carrying a chemically selective coating which is suspended by an elastic element above an orifice in an insulated substrate.

28. The system of claim 27 wherein the valve is electrostatically actuatable.

29. The system of claim 26 wherein the second stage operatively provides a defined fixed volume within the trap into which a heating of the sorbent material of the second stage provides a concentrated slug of analyte species for subsequent provision into the detector for analysis and identification.

30. A detector system comprising a detector coupled to a first and second pre-concentrator stage, each of the first and second pre-concentrator stages having a sorbent material to collect samples, and wherein the first pre-concentrator stage is removable from the detector so as to be portable to enable a collection of a sample within the first pre-concentrator stage at a location remote from the detector, and further wherein coupling of the first pre-concentrator stage to the detector defines a fluid path from the first pre-concentrator stage to the second pre-concentrator stage to the detector, the second pre-concentrator stage including a trap having an orifice through which a gas may flow, the orifice being controlled by a valve, which is moveable between a first position, wherein the gas is free to move through the orifice from the first pre-concentrator stage and into the trap, and a second position wherein the valve seals the orifice preventing the flow of gas into the trap, and wherein the sorbent material is provided in the trap to sorb the species present in the gas during the flow of gas through the trap.

* * * * *